United States Patent
Thakur et al.

(10) Patent No.: US 10,016,145 B2
(45) Date of Patent: Jul. 10, 2018

(54) FAR-FIELD VS LOCAL ACTIVATION DISCRIMINATION ON MULTI-ELECTRODE EGMS USING VECTOR ANALYSIS IN MULTI-DIMENSIONAL SIGNAL SPACE

(71) Applicant: Boston Scientific Scimed, Inc., Maple Grove, MN (US)

(72) Inventors: Pramodsingh Hirasingh Thakur, Woodbury, MN (US); Barun Maskara, Blaine, MN (US); Allan C. Shuros, St. Paul, MN (US); Sunipa Saha, Shoreview, MN (US); Shibaji Shome, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 961 days.

(21) Appl. No.: 13/923,020

(22) Filed: Jun. 20, 2013

(65) Prior Publication Data

US 2013/0345537 A1 Dec. 26, 2013

Related U.S. Application Data

(60) Provisional application No. 61/662,252, filed on Jun. 20, 2012.

(51) Int. Cl.
*A61B 5/042* (2006.01)
*A61B 5/04* (2006.01)
(Continued)

(52) U.S. Cl.
CPC ............ *A61B 5/0422* (2013.01); *A61B 5/042* (2013.01); *A61B 5/0044* (2013.01); *A61B 5/0402* (2013.01);
(Continued)

(58) Field of Classification Search
CPC ..... A61B 5/0044; A61B 5/042; A61B 5/0422; A61B 5/04007; A61B 5/0402;
(Continued)

(56) References Cited

U.S. PATENT DOCUMENTS 4,407,296 A 10/1983 Anderson
4,962,767 A 10/1990 Brownlee
(Continued)

FOREIGN PATENT DOCUMENTS

CN 1253761 A 5/2000
CN 200960161 Y 10/2007
(Continued)

OTHER PUBLICATIONS

International Preliminary Report on Patentability issued in PCT/US2013/076958, dated Jun. 30, 2015, 8 pages.
(Continued)

*Primary Examiner* — Timothy J Neal
*Assistant Examiner* — Aaron B Fairchild
(74) *Attorney, Agent, or Firm* — Faegre Baker Daniels LLP

(57) ABSTRACT

Electrical activity propagation along an electrode array within a cardiac chamber is reconstructed. Signals are sampled from the electrode array and the signals are plotted in multi-dimensional space with each axis corresponding to a channel in the electrode array. An excursion direction of global activation in the multi-dimensional space is estimated and a change in vectors of the sampled signals over time is determined. Signals with vectors that change over time in the excursion direction are suppressed.

9 Claims, 4 Drawing Sheets

(51) Int. Cl.
   *A61B 5/00* (2006.01)
   *A61B 18/14* (2006.01)
   *A61B 5/0402* (2006.01)

(52) U.S. Cl.
   CPC ....... *A61B 5/04007* (2013.01); *A61B 5/04012* (2013.01); *A61B 5/6859* (2013.01); *A61B 18/1492* (2013.01)

(58) Field of Classification Search
   CPC . A61B 5/0412; A61B 5/6859; A61B 18/1492; A61B 5/04012
   USPC .............................. 600/374, 509, 512, 513
   See application file for complete search history.

(56) References Cited

U.S. PATENT DOCUMENTS

| | | |
|---|---|---|
| 5,161,539 A | 11/1992 | Evans et al. |
| 5,647,870 A | 7/1997 | Kordis et al. |
| 5,683,425 A | 11/1997 | Hauptmann |
| 5,772,693 A | 6/1998 | Brownlee |
| 5,776,072 A | 7/1998 | Hsu et al. |
| 5,782,898 A | 7/1998 | Dahl et al. |
| 5,817,133 A | 10/1998 | Houben |
| 6,070,094 A | 5/2000 | Swanson et al. |
| 6,214,025 B1 | 4/2001 | Thistle et al. |
| 6,233,491 B1 | 5/2001 | Kordis et al. |
| 6,650,931 B1 | 11/2003 | McClure et al. |
| 6,660,021 B1 | 12/2003 | Palmer et al. |
| 6,735,465 B2 | 5/2004 | Panescu |
| 6,810,283 B2 | 10/2004 | Suribhotla et al. |
| 7,338,512 B2 | 3/2008 | McGuckin, Jr. et al. |
| 7,672,722 B1 | 3/2010 | Mengotto |
| 7,780,694 B2 | 8/2010 | Palmer et al. |
| 7,850,708 B2 | 12/2010 | Pal |
| 7,933,643 B1 | 4/2011 | Gill et al. |
| 8,019,409 B2 | 9/2011 | Rosenberg et al. |
| 8,055,333 B2 | 11/2011 | Duann et al. |
| 8,060,202 B2 | 11/2011 | Betzold et al. |
| 8,090,434 B2 | 1/2012 | Lian et al. |
| 8,155,739 B2 | 4/2012 | Keel et al. |
| 8,165,666 B1 | 4/2012 | Briggs et al. |
| 8,175,693 B2 | 5/2012 | Rosenberg et al. |
| 8,195,292 B2 | 6/2012 | Rosenberg et al. |
| 8,543,195 B1 | 9/2013 | Brockway et al. |
| 9,131,866 B2 | 9/2015 | Thakur et al. |
| 2003/0212336 A1 | 11/2003 | Lee et al. |
| 2003/0236466 A1 | 12/2003 | Tarjan et al. |
| 2004/0039293 A1 | 2/2004 | Porath et al. |
| 2004/0176694 A1 | 9/2004 | Kim et al. |
| 2005/0154321 A1 | 7/2005 | Wolinsky et al. |
| 2005/0209678 A1 | 9/2005 | Henkes et al. |
| 2005/0288600 A1 | 12/2005 | Zhang et al. |
| 2006/0069322 A1* | 3/2006 | Zhang ................... A61B 5/7203 600/512 |
| 2006/0116595 A1 | 6/2006 | Palreddy et al. |
| 2006/0253044 A1 | 11/2006 | Zhang et al. |
| 2008/0071182 A1* | 3/2008 | Cazares ................ A61B 5/0464 600/509 |
| 2008/0109041 A1 | 5/2008 | de Voir |
| 2008/0243214 A1 | 10/2008 | Koblish |
| 2008/0281369 A1 | 11/2008 | KenKnight et al. |
| 2009/0240157 A1 | 9/2009 | Lian et al. |
| 2009/0254140 A1 | 10/2009 | Rosenberg et al. |
| 2009/0306732 A1 | 12/2009 | Rosenberg et al. |
| 2009/0318995 A1 | 12/2009 | Keel et al. |
| 2010/0152801 A1 | 6/2010 | Koh et al. |
| 2010/0256699 A1 | 10/2010 | Makdissi |
| 2010/0268059 A1 | 10/2010 | Ryu et al. |
| 2011/0054559 A1 | 3/2011 | Rosenberg et al. |
| 2011/0054560 A1 | 3/2011 | Rosenberg et al. |
| 2011/0066201 A1 | 3/2011 | Rosenberg et al. |
| 2011/0066202 A1 | 3/2011 | Rosenberg et al. |
| 2011/0066203 A1 | 3/2011 | Rosenberg et al. |
| 2011/0092809 A1 | 4/2011 | Nguyen et al. |
| 2011/0118803 A1 | 5/2011 | Hou et al. |
| 2011/0144510 A1 | 6/2011 | Ryu et al. |
| 2011/0184274 A1 | 7/2011 | Rosenberg et al. |
| 2011/0213260 A1 | 9/2011 | Keel et al. |
| 2011/0251505 A1 | 10/2011 | Narayan et al. |
| 2011/0295137 A1 | 12/2011 | Rosenberg et al. |
| 2011/0319954 A1 | 12/2011 | Niazi et al. |
| 2012/0157865 A1 | 6/2012 | Stein et al. |
| 2012/0184863 A1 | 7/2012 | Harlev et al. |
| 2012/0327204 A1 | 12/2012 | Friedman et al. |
| 2013/0116577 A1 | 5/2013 | Yazicioglu et al. |
| 2013/0274582 A1 | 10/2013 | Afonso et al. |
| 2013/0345577 A1 | 12/2013 | Thakur et al. |
| 2013/0345583 A1 | 12/2013 | Thakur et al. |
| 2014/0018792 A1 | 1/2014 | Gang et al. |
| 2014/0067279 A1 | 3/2014 | George et al. |
| 2014/0187991 A1 | 7/2014 | Thakur et al. |
| 2014/0316294 A1 | 10/2014 | Maskara et al. |
| 2015/0257671 A1 | 9/2015 | Laughner et al. |
| 2015/0342536 A1 | 12/2015 | Kovtun et al. |

FOREIGN PATENT DOCUMENTS

| | | |
|---|---|---|
| CN | 101365379 A | 2/2009 |
| CN | 10558993 A | 10/2009 |
| EP | 1543865 A1 | 6/2005 |
| EP | 2863792 A1 | 4/2015 |
| EP | 2863793 A1 | 4/2015 |
| JP | H11511666 A | 10/1999 |
| JP | 2005501674 A | 1/2005 |
| JP | 2006025836 A | 2/2006 |
| JP | 2010522623 A | 7/2010 |
| JP | 2013523344 A | 6/2013 |
| JP | 2014502556 A | 2/2014 |
| WO | WO2000045700 A1 | 8/2000 |
| WO | WO2000047278 A1 | 8/2000 |
| WO | WO2011041489 A2 | 4/2001 |
| WO | WO03022356 A2 | 3/2003 |
| WO | WO2006037172 A1 | 4/2006 |
| WO | WO2008118992 A1 | 10/2008 |
| WO | WO2011075328 A1 | 6/2011 |
| WO | 2012097059 A1 | 7/2012 |
| WO | 2014058484 A1 | 4/2014 |
| WO | 2015187371 A1 | 12/2015 |

OTHER PUBLICATIONS

International Search Report and Written Opinion issued in PCT/US2013/076958, dated Apr. 7, 2014, 14 pages.

International Search Report and Written Opinion issued in PCT/US2015/031787, dated Aug. 5, 2015, 11 pages.

International Search Report and Written Opinion issued in International Application No. PCT/US2013/046843, dated Oct. 23, 2013, 12 pages.

International Search Report and Written Opinion issued in PCT/US2013/046841, dated Oct. 15, 2013, 12 pages.

Potter, M. et al., "Competing ICA Techniques in Biomedical Signal Analysis", Electrical and Computer Engineering, 2001, Canadian Conference on May 13-16, 2001, Piscataway, NJ, USA, IEEE, vol. 2, May 13, 2001, pp. 987-992.

Zhou, Yu et al., "A New United Analysis Method for Epicardial Mapping Signals", Bioinformatics and Biomedical Engineering, 2008, ICBBE 2008, the Second International Conference, IEEE, Piscataway, NJ, USA, May 16, 2008, pp. 636-639.

* cited by examiner

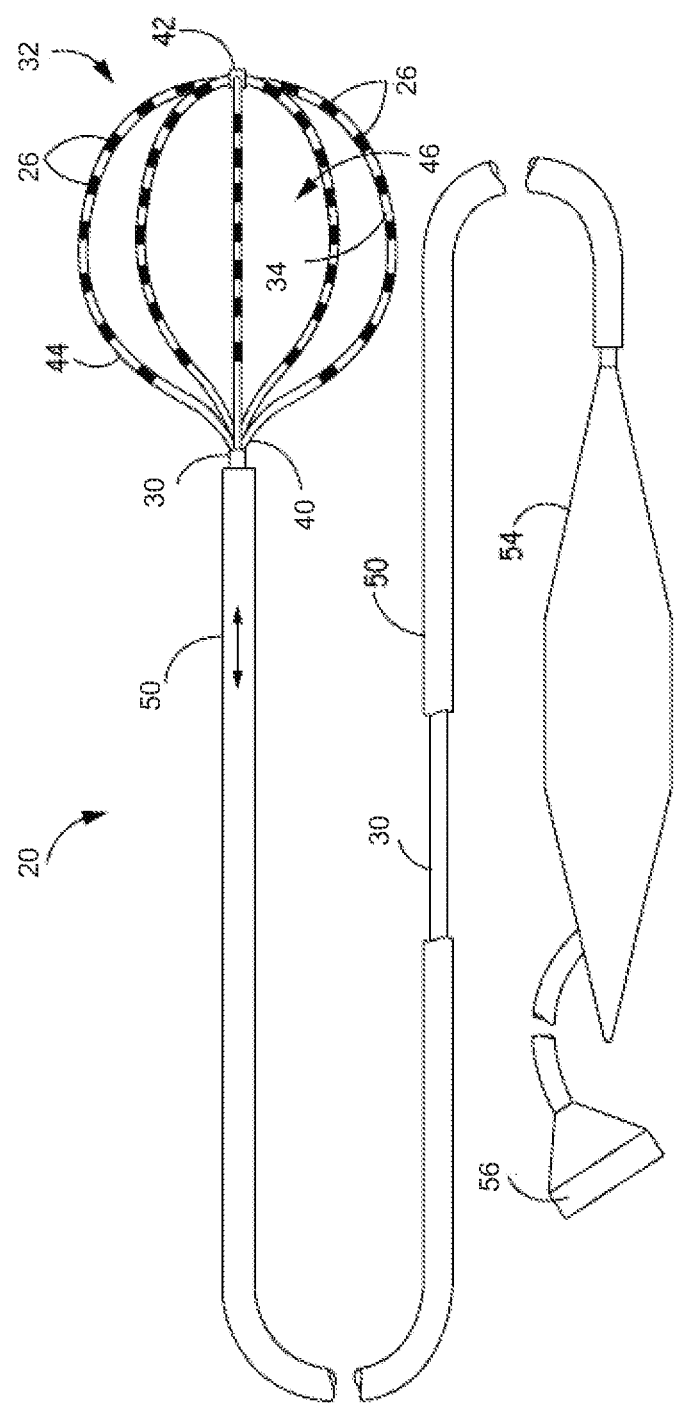

FAR-FIELD VS LOCAL ACTIVATION DISCRIMINATION ON MULTI-ELECTRODE EGMS USING VECTOR ANALYSIS IN MULTI-DIMENSIONAL SIGNAL SPACE

CROSS-REFERENCE TO RELATED APPLICATION

This application claims priority to Provisional Application No. 61/662,252, filed Jun. 20, 2012, which is herein incorporated by reference in its entirety.

TECHNICAL FIELD

The present disclosure relates to cardiac mapping systems. More particularly, the present disclosure relates to a cardiac mapping system configured to reconstruct electrical activity propagation along an electrode array within a cardiac chamber of interest by preserving local activity and suppressing far-field activity.

BACKGROUND

Diagnosing and treating heart rhythm disorders often involves the introduction of a catheter having a plurality of sensors/probes into the heart through the blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat in timing and often in shape and number of its deflections, enabling identification of activation onsets at each sensor location. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are at or near the sensor location in the heart (i.e., local activation) versus a further removed location still sensed by the sensor in the heart (i.e., far-field activation) or simply noise from another part of the patient's heart, other anatomic structures, movement or motion of the sensor relative to the heart or external electronic systems.

SUMMARY

Disclosed herein are various embodiments of a method for discriminating between local activation signals and far-field activity in a cardiac mapping system, as well as cardiac mapping systems employing such methods.

In Example 1, a method for reconstructing electrical activity propagation along an electrode array within a cardiac chamber includes sampling signals from the electrode array and plotting the signals in multi-dimensional space with each axis corresponding to a channel in the electrode array. The method also includes estimating an excursion direction of global activation in the multi-dimensional space and determining a change in vectors of the sampled signals over time. The method further includes suppressing signals with vectors that change over time in the excursion direction.

In Example 2, the method according to Example 1, wherein plotting the signals further includes shifting each sampled signal by an expected latency of a corresponding far-field signal sampled from the electrode array based on a reference signal.

In Example 3, the method according to either Example 1 or Example 2, wherein the estimating step comprises normalizing the sampled signals to match scales.

In Example 4, the method according to any of Examples 1-3, wherein the determining step comprises determining an absolute time derivative of the vectors.

In Example 5, the method according to any of Examples 1-4, wherein the estimating step comprises determining a maximum eigenvalue of a decomposition of the plotted signals.

In Example 6, the method according to any of Examples 1-5, wherein the estimating step further comprises blanking signals around significant excursions along each axis (local activation).

In Example 7, the method according to any of Examples 1-6, wherein sampling the signals comprises including channels designed or biased toward picking up global activity in the multi-dimensional space to enhance discrimination on other channels.

In Example 8, the method according to any of Examples 1-7, wherein sampling the signals comprises employing an extended bipolar configuration with the electrode array.

In Example 9, the method according to any of Examples 1-8, wherein employing an extended bipolar configuration comprises sampling signals from most opposed electrodes located on the electrode array.

In Example 10, a method for reconstructing electrical activity propagation along an electrode array within a cardiac chamber includes sampling signals from the electrode array and plotting the signals in multi-dimensional space with each axis corresponding to a channel in the electrode array. The method also includes determining a change in vectors of the sampled signals over time and comparing the time change in vectors of the sampled signals with unit vectors along each axis in the multi-dimensional space. The method further includes suppressing signals with vectors that do not correspond to the unit vector of one of the axes.

In Example 11, a mapping system including an electrode array is configured to reconstruct electrical activity propagation within a cardiac chamber according to the method of any of Examples 1-9.

In Example 12, a mapping system for reconstructing electrical activity propagation within a cardiac chamber includes an array of mapping electrodes configured to sample signals from a channel of interest, and a processing device associated with the plurality of mapping electrodes, the processing device configured to record the sampled signals and associate one of the plurality of mapping electrodes with each recorded signal, the mapping processor further configured to sampling signals from the array of mapping electrodes, plot the signals in multi-dimensional space with each axis corresponding to a channel in the array of mapping electrodes, estimate an excursion direction of global activation in the multi-dimensional space, determine a change in vectors of the sampled signals over time, and suppress signals with vectors that change over time in the excursion direction.

In Example 13, the mapping system according to Example 12, wherein to plot the signals further includes shifting each sampled signal by an expected latency of a corresponding far-field signal sampled from the electrode array based on a reference signal.

In Example 14, the mapping system according to either Example 12 or Example 13, wherein to estimate an excursion direction, the processing device is further configured to normalize the sampled signals to match scales.

In Example 15, the mapping system according to any of Examples 12-14, wherein to determine a change in vectors, the processing system is further configured to determine an absolute time derivative of the vectors.

In Example 16, the mapping system according to any of Examples 12-15, wherein to estimate an excursion direction, the processing device is further configured to determine a maximum eigenvalue of a decomposition of the plotted signals.

In Example 17, the mapping system according to any of Examples 12-16, the processing device is further configured to blank signals around significant excursions along each axis (local activation).

In Example 18, the mapping system according to any of Examples 12-17, wherein to sample the signals, the processing system is further configured to bias a subset of channels towards picking up global activity in the multi-dimensional space to enhance discrimination on other channels.

In Example 19, the mapping system according to any of Examples 12-18, wherein to sample the signals, the processing device is further configured to employ an extended bipolar configuration on the array of mapping electrodes.

In Example 20, the mapping system according to any of Examples 12-19, wherein the processing device is further configured to employ the extended bipolar configuration at the most opposed electrodes located on the array of mapping electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 illustrates an embodiment of a mapping catheter having a basket functional element carrying structure.

Figure 1:
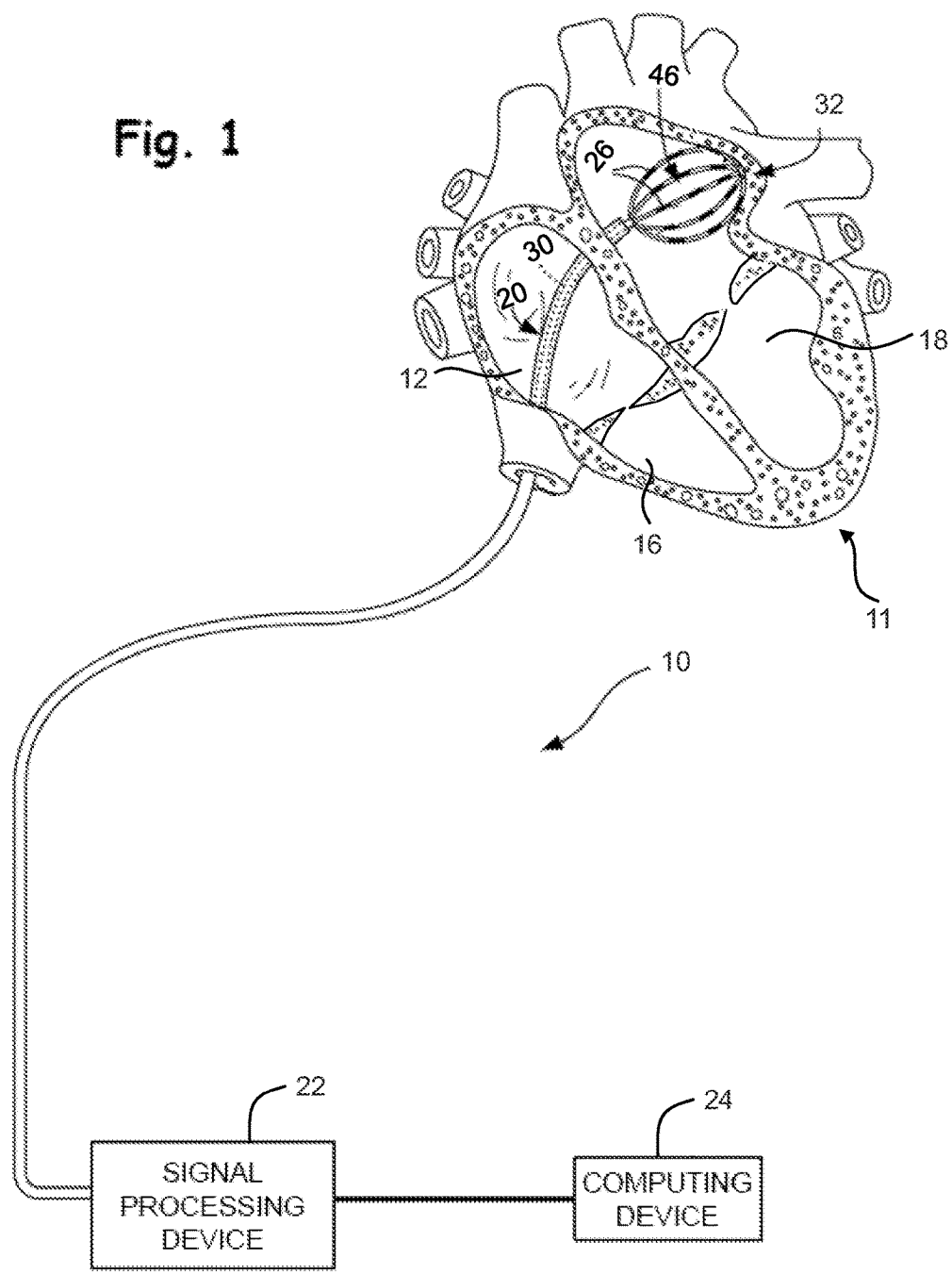
FIG. 1 illustrates an embodiment of a cardiac activation reconstruction system according to the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an embodiment of a cardiac activation reconstruction system 10. The system 10 is configured to detect and reconstruct cardiac activation information collected/detected from a patient's heart 11 in connection with a heart rhythm disorder. The heart includes a right atrium 12, left atrium 14, right ventricle 16 and left ventricle 18.

The system 10 includes a catheter 20, a signal processing device 22, and a computing device 24. The catheter 20 is configured to detect cardiac activation information in the heart and to transmit the detected cardiac activation information to the signal processing device 22, either via a wireless or wired connection. The distal end of the catheter 20 includes a plurality of sensors 26, which can be inserted into the heart through the patient's blood vessels.

In some embodiments, one or more of sensors are not inserted into the patient's heart. For example, some sensors may detect cardiac activation via the patient's surface (e.g., electrocardiogram) or remotely without contact with the patient (e.g., magnetocardiogram). As another example, some sensors may also derive cardiac activation information from cardiac motion of a non-electrical sensing device (e.g., echocardiogram). In various embodiments or aspects, these sensors can be used separately or in different combinations, and further these separate or different combinations can also be used in combination with sensors inserted into the patient's heart.

The sensors 26, which are positioned at sensor locations in the heart under consideration (e.g., the left atrium in the illustrated embodiment), can detect cardiac activation information at the sensor locations. In some embodiments, an integral ablation electrode or a separate ablation catheter may be used to deliver energy to ablate the heart at or proximate the sensor locations.

The signal processing device 22 is configured to process (e.g., clarify and amplify) the cardiac activation information detected by the sensors 26 at the sensor locations into electrogram signals and to provide the processed cardiac signals to the computing device 24 for analysis or processing in accordance with various methods, such as those disclosed herein.

FIG. 2 illustrates an embodiment of a mapping catheter 20 including sensors at the distal end suitable for use in the system 10 shown in FIG. 1. The mapping catheter 20 that has a flexible catheter body 30, the distal end of which carries a three dimensional structure 32 configured to carry a plurality of mapping elements or sensors 26. In some embodiments, a proximity element 34 is preferably located adjacent each mapping element 26. Alternatively, the mapping elements 26 can be used as the proximity elements 34. As will be described in further detail below, the mapping elements 26 sense electrical activity in the heart tissue, which sensed activity is then processed by the signal processing device 22 and computing device 24 to assist the physician in identifying the site or sites having a heart rhythm disorder. This process is commonly referred to as mapping. This information can then be used to determine an appropriate location for applying appropriate therapy (e.g., ablation) to the identified sites.

The illustrated three dimensional structure 32 comprises a base member 40 and an end cap 42 between which flexible splines 44 generally extend in a circumferentially spaced relationship. As illustrated, the three dimensional structure 32 takes the form of a basket defining an open interior space 46. In some embodiments, the splines 44 are made of a resilient inert material, such as, e.g., Nitinol metal or silicone rubber, and are connected between the base member 40 and the end cap 42 in a resilient, pretensed condition, to bend and conform to the tissue surface they contact. In the illustrated embodiment, eight splines 44 form the three dimensional structure 32. Additional or fewer splines 44 could be used in other embodiments. As illustrated, each spline 44 carries eight mapping elements 26. Additional or fewer mapping elements 26 could be disposed on each spline 44 in other embodiments of the three dimensional structure 32. In the illustrated embodiment, the three dimensional structure 32 is relatively small (e.g., 40 mm or less in diameter). In alternative embodiments, the three dimensional structure 32 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 32, thereby collapsing the structure 32 into a compact, low profile condition suitable for introduction into an interior space, such as, for example, into the heart 12. In contrast, moving the sheath 19 rearward (i.e., toward the proximal end) frees the three dimensional structure 32, allowing the structure 32 to spring open and assume the pretensed position illustrated in FIG. 2. Further details of embodiments of the three dimensional structure 20 are disclosed in U.S. Pat. No. 5,647,870, entitled "Multiple Electrode Support Structures," the disclosure of which is expressly and fully incorporated by reference.

A signal wire (not shown) is electrically coupled to each mapping element 26. The wires extend through the body 30 of the mapping catheter 20 into a handle 54, in which they are coupled to an external connector 56, which may be a multiple pin connector. The connector 56 electrically couples the mapping elements 26 to the signal processing device 22 and computing device 24. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are expressly and fully incorporated herein by reference. In a similar manner, a signal wire electrically couples each proximity element 34 to the signal processing device 22 and computing device 24.

It is noted that other three dimensional structures could be deployed on the distal end. It is further noted that the multiple mapping elements 26 may be disposed on more than one structure rather than, for example, the single mapping catheter 20 illustrated in FIG. 2. For example, if mapping within the left atrium 14 with multiple mapping structures, an arrangement comprising a coronary sinus catheter carrying multiple mapping elements and a basket catheter carrying multiple mapping elements positioned in the left atrium 14 may be used. As another example, if mapping within the right atrium 12 with multiple mapping structures, an arrangement comprising a decapolar catheter carrying multiple mapping elements for positioning in the coronary sinus, and a loop catheter carrying multiple mapping elements for positioning around the tricuspid annulus may be used.

Additionally, although the mapping elements 26 have been described as being carried by mapping dedicated probes, such as mapping catheter 20, mapping elements can be carried on non-mapping dedicated probes. For example, an ablation catheter can be configured to include one or mapping elements disposed on the distal end of the catheter body 30 and coupled to the signal processing device 22 and computing device 24. As another example, the ablation electrode at the distal end of the ablation catheter may be coupled to the signal processing device 22 and computing device 24 to also operate as a mapping electrode.

Figure 3A:
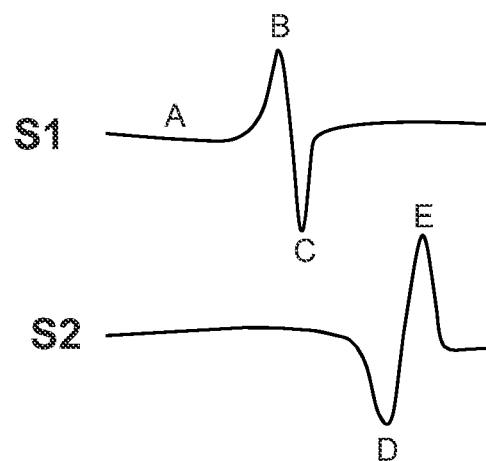
FIG. 3A illustrates an example of a plot of two channels from mapping elements of the basket functional element as a function of time.
Figure 3B:
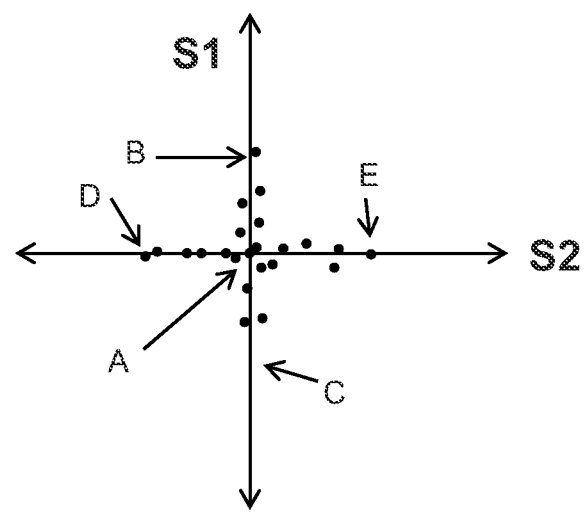
FIG. 3B illustrates an example of a plot using signals of two channels in the array of mapping elements in two-dimensional space.

In various embodiments, signals sensed by mapping elements 26 can be plotted to generate a multi-dimensional representation of signals from multiple elements or channels. FIG. 3A illustrates an example of a plot of two channels (S1, S2) from the mapping elements 26 as a function of time. For example, in the embodiment illustrated in FIG. 2, channels S1 and S2 may be signals from a selected two of the sixty-four mapping elements 26. FIG. 3B illustrates an example of a plot using signals from two channels in the array of mapping elements 26 in two-dimensional space, with signal samples at various points in time for channel S1 plotted along the vertical axis and signal samples at various points in time for channel S2 plotted along the horizontal axis. The signals from channel S1 at points in time A, B, and C shown in FIG. 3A are shown plotted in FIG. 3B along the vertical axis, the signals from channel S2 at points in time D and E in FIG. 3A are shown plotted in FIG. 3B along the horizontal axis. While two channels are shown, any number of channels may be plotted to generate a multi-dimensional (or, N-dimensional) representation of signals from a corresponding number of channels.

According to the present disclosure, the N-dimensional representation of signals can be processed by the signal processing device 22 and/or computing device 24 to suppress signals due to global activation (i.e., far-field activity) to enhance signals associated with local activation. In the N-dimensional representation, global activation may be characterized by excursions along certain directions in the N-dimensional space. To facilitate suppression of these signals, the direction of a unit vector $U_{CM}$ in the direction of the global activation excursions may be estimated. Then, the vector representation of signals on the channels S of the three dimensional structure 32 at time t can be defined as:

$$V(t)=[S1(t),S2(t),S3(t),\ldots,SN(t)]^T \quad \text{(Equation 1)}$$

Global activations will cause signal excursions along (i.e., parallel to) $U_{CM}$ such that V(t) will change along $U_{CM}$ in N-dimensional space. Thus, the signal processing device 22 and/or computing device 24 may take the time derivative of V(t) to characterize the time variation of the signal. This result may projected onto $U_{CM}$ and compared to a predetermined threshold:

$$\frac{\frac{dV(t)^T}{dt} * U_{CM}}{\left\|\frac{dV(t)}{dt}\right\|} > TH$$

Figure 4:
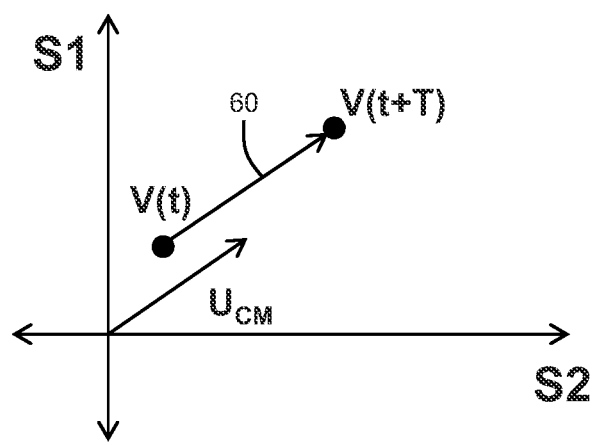
FIG. 4 illustrates a plot of a signal of a channel at times t and t+T with the resulting vector extending in parallel to the direction of global activations, indicating far-field activation of the channel.

In other words, if the derivative of V(t) substantially similar to the slope/direction $U_{CM}$, the change in the signal may be due to global activations, and the inequality above would be true. The equation stated above represents one way of comparing the direction of the excursion of signal vector change in multi-dimensional space with the direction of global activation ($U_{CM}$). Other ways of comparison may include using the signal vector change ($\Delta V(t)$) rather than the derivative or calculating an angle between the two vectors in the N-dimensional space. FIG. 4 illustrates a vector 60 connecting a signal change between channels S1 and S2 at time t and time t+T, wherein the vector 60 is substantially parallel to the unit vector $U_{CM}$. Thus, the signal change between time t and t+T can be attributed to global activations. During processing, signal processing device 22 and/or computing device 24 may be configured to suppress these signals.

Figure 5:
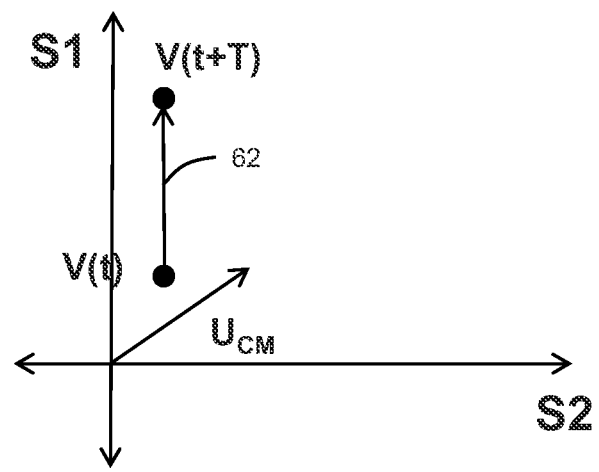
FIG. 5 illustrates a plot of a signal of a channel at times t and t+T with the resulting vector extending non-parallel to the direction of global activations, indicating local activation of the channel.

If the derivative of V(t) is not equal to the slope/direction $U_{CM}$, the change in the signal is likely due to local activations, and the inequality above would not be true. FIG. 5 illustrates a vector 62 connecting a signal change between channels S1 and S2 at time t and time t+T, wherein the vector 62 is not parallel to the unit vector $U_{CM}$. Rather, the vector 62 is substantially parallel to the axis S1, indicating that the change is due to a local activation at or near the channel S1.

In some instances, the far-field signal may not appear instantaneously on all channels, but may exhibit a characteristic delay or a latency associated with volume propagation characteristic of the far-field component propagating through tissue. In scenarios where latencies are identified and/or expected, both Equation 1 and Equation 2 can be modified to account for the latencies associated with various electrodes. For example, if far-field signals emerge at latencies of $\omega_1, \omega_2, \ldots, \omega_N$ over the N neighboring electrodes with respect to a far-field reference signal such as a surface ECG, Equation 2 can be expressed as:

$$V(t) = [S_0(t) - S_1(t+\omega_1), S_0(t) - S_2(t+\omega_2), \ldots, S_0(t) - S_N(t+\omega_N)]^T \quad \text{(Equation 3)}$$

The latencies can be estimated by tracking the peaks or other characteristic features of the far-field signal on each channel with respect to the peaks or other characteristic feature of the corresponding R-wave sensed by the surface ECG. The estimated latencies can be averaged over multiple local heart beats.

Various approaches to estimating the unit vector $U_{CM}$ and subsequently suppressing the global activations may be taken. For example, assume the unit vector $U_{CM}$ of global activations can be represented as a unity slope line in N-dimensional space:

$$U_{CM} = \left[\frac{1}{\sqrt{N}}, \frac{1}{\sqrt{N}}, \ldots, \frac{1}{\sqrt{N}}\right]^T \quad \text{(Equation 2)}$$

Equation 2 assumes that global activation has similar scales on all channels from the mapping elements 26. The scales of each channel may then be normalized with respect to each other:

$$V(t) = \left[\frac{S1(t)}{\|S1\|}, \frac{S2(t)}{\|S2\|}, \ldots, \frac{SN(t)}{\|SN\|}\right]^T \quad \text{(Equation 3)}$$

Excursions are in-phase on all channels S1-SN. In some embodiments, the absolute derivative of V(t) may be considered instead of the inequality above:

$$\frac{\text{abs}\left(\frac{dV(t)}{dt}\right)^T * U_{CM}}{\left\|\frac{dV(t)}{dt}\right\|} > TH$$

As another example, $U_{CM}$ may be estimated by first blanking signals around significant excursions along each axis (i.e., local activations). The signal processing device 22 and/or computing device 24 may then process the data associated with the remainder data set to suppress the correlated data. In some embodiments, the signal processing device 22 and/or computing device 24 performs an eigenvector/eigenvalue decomposition of a covariance matrix of the remainder data set, which characterizes the variation/spread of the data in the two-dimensional space. The eigenvector corresponding to the largest eigenvalue points to the direction of maximum elongation in the remainder data set, which is essentially $U_{CM}$.

In some embodiments, the channels (e.g., channels S1 and S2) sampled may be selected to bias toward picking up global activity in the N-dimensional space to enhance discrimination on other channels. For example, mapping elements 26 distal from the tissue may be referenced to other elements that generate far field interference to help with discriminating between far-field and local activations. In some embodiments, the selected channels may be the most opposed electrodes located on the three dimensional structure 32 to assess global atrial activity (i.e., extended bipolar configuration).

An alternative approach to suppressing excursions due to global activation is to compare the derivative of V(t) to unit vectors along each axis in N-dimensional space. Since local activation is expected to cause a signal excursion along the axis corresponding to the locally activated channel, a signal vector extending in parallel to one of these unit vectors indicates local activation. Thus, if $E_{Si}$ is a unit vector along channel $S_i$ and $E_{Sj}$ is the unit vector along channel $S_j$, the following can be used to determine whether a signal vector is due to local or global activations:

$$\frac{\frac{dV(t)^T}{dt} * E_{Si}}{\left\|\frac{dV(t)}{dt}\right\|} > TH1 \ \& \ \frac{\frac{dV(t)^T}{dt} * E_{Sj}}{\left\|\frac{dV(t)}{dt}\right\|} < TH2 \forall \ j \neq i$$

In this mathematical statement, the unit vectors $E_{Si}$ and $E_{Sj}$ are normalized with respect to the time derivative of V(t) and compared with thresholds TH1 and TH2. If this mathematical statement is satisfied, this indicates that an excursion along the axis associated with channel $S_i$, which is indicative of local activation on channel $S_i$. Corollary mathematical statements may be generated to indicate excursions along the axis associated with channel $S_j$, and excursions due to global activations.

The method and system as described provides a flexible mathematical framework that can work with any number of channels on a mapping catheter (e.g., neighboring 8, neighboring 16, all at once, two groups of local and far-field). The ability to process information from any number of channels provides a more faithful reconstruction of electrical activity propagation in the chamber of interest compared to conventional paired channel comparisons for discriminating far-field activity from local activity.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for reconstructing electrical activity propagation along an electrode array within a cardiac chamber, the method comprising:
    receiving, by a computing device, cardiac signals corresponding to cardiac activation information sensed by the electrode array;
    generating a multi-dimensional representation of the cardiac signals by plotting, using the computing device, the cardiac signals in multi-dimensional space with each dimension corresponding to a channel in the electrode array;
    estimating, using the computing device, an excursion direction of global activation in the multi-dimensional space;
    defining, using the computing device, a vector representation of the cardiac signals;
    determining, using the computing device, a signal change, corresponding to an identified time period, between a first channel and a second channel;
    determining, using the computing device, that the signal change is attributable to global activation by comparing an excursion direction of the signal change with the excursion direction of global activation;
    suppressing, using the computing device, the cardiac signals, during the identified time period, corresponding to the signal change;
    generating, using the computing device, a reconstruction of cardiac electrical activity propagation based on the cardiac signals that are not suppressed; and
    displaying, on a display device, the reconstruction of cardiac electrical activity propagation.

2. The method of claim 1, wherein plotting the cardiac signals further includes:
    shifting each cardiac signal by an expected latency of a corresponding far-field signal received from the electrode array based on a reference signal.

3. The method of claim 1, wherein estimating an excursion direction further comprises:
    normalizing the cardiac signals to match scales.

4. The method of claim 1, wherein determining the signal change further comprises:
    determining an absolute time derivative of the vector representation.

5. The method of claim 1, wherein estimating an excursion direction further comprises:
    determining a maximum eigenvalue of a decomposition of the plotted signals.

6. The method of claim 5, further comprising:
    blanking cardiac signals around significant excursions along each axis (local activation).

7. The method of claim 1, wherein receiving the signals further comprises:
    biasing a subset of channels towards picking up global activity in the multi-dimensional space to enhance discrimination on other channels.

8. The method of claim 1, wherein receiving the signals comprises employing an extended bipolar configuration with the electrode array.

9. The method of claim 8, wherein employing an extended bipolar configuration comprises receiving signals from most opposed electrodes located on the electrode array.

* * * * *